United States Patent
Deng et al.

(10) Patent No.: US 10,274,474 B2
(45) Date of Patent: Apr. 30, 2019

(54) SYSTEM AND METHOD FOR CONNECTING AN EXTERNAL DEVICE TO A GAS DETECTOR

(71) Applicant: Honeywell International Inc., Morris Plains, NJ (US)

(72) Inventors: Liandong Deng, Shanghai (CN); Yong Tang, Shanghai (CN); Rui Feng, Kunshan (CN)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/637,994

(22) Filed: Jun. 29, 2017

(65) Prior Publication Data

US 2019/0004022 A1    Jan. 3, 2019

(51) Int. Cl.
*G01N 1/22* (2006.01)
*G01N 33/00* (2006.01)

(52) U.S. Cl.
CPC ..... *G01N 33/0075* (2013.01); *G01N 33/0008* (2013.01); *G01N 33/0067* (2013.01); *G01N 2001/2276* (2013.01)

(58) Field of Classification Search
CPC .................. G01N 33/0075; G01N 33/0008
USPC .......................................................... 340/632
See application file for complete search history.

(56) References Cited

U.S. PATENT DOCUMENTS

| | | | |
|---|---|---|---|
| 4,892,380 A * | 1/1990 | Mori | G02B 6/3825 385/58 |
| 7,180,076 B2 | 2/2007 | Haverstick et al. | |
| 9,212,966 B2 | 12/2015 | Scheucher | |
| 2002/0197907 A1* | 12/2002 | Divine | H01R 13/518 439/505 |
| 2003/0224643 A1* | 12/2003 | Starta | H01R 13/527 439/246 |
| 2004/0018775 A1* | 1/2004 | Mazzullo | H01R 13/4534 439/676 |
| 2005/0000271 A1* | 1/2005 | Rabenecker | G01N 33/0009 73/23.2 |
| 2010/0158758 A1* | 6/2010 | Gustin | F01N 13/008 422/83 |

(Continued)

OTHER PUBLICATIONS

Shenzhen Indus-Connector, Waterproof 3 pin, 4 pin, 5 pin, 8 pin, 12 pin, m12 connector, 5 pages, [retrieved on Apr. 5, 2017] Retrieved from the Internet: URL<https://indus-connector.en.alibaba.com/product/1622433195-803704524/Waterproof_ 3_pin_4pin_5_pin_8_pin_12_pin_m12_connector.html?spsm=a2700.8304367>.

*Primary Examiner* — Kerri L McNally
(74) *Attorney, Agent, or Firm* — Wick Phillips Gould & Martin, LLP

(57) ABSTRACT

Embodiments relate generally to systems and methods for providing a secure attachment between a gas detector and an external device. A gas detector may comprise a socket comprising a cable attachment configured to interface with an external device; and a holder configured to attach to the socket and to the external device, the holder comprising a first interface configured to attach to the socket of the gas detector; a second interface configured to attach to the external device; a first cable attachment located within the first interface, configured to attach to the gas detector; and a second cable attachment located within the second interface, configured to attach to the external device.

18 Claims, 6 Drawing Sheets

(56) References Cited

U.S. PATENT DOCUMENTS

| | | | |
|---|---|---|---|
| 2014/0257127 A1* | 9/2014 | Smith | A61B 5/082 |
| | | | 600/532 |
| 2015/0377658 A1* | 12/2015 | Landis | G01D 11/245 |
| | | | 439/660 |
| 2016/0005507 A1* | 1/2016 | Al Ammar | H01B 7/04 |
| | | | 174/74 R |
| 2018/0095061 A1* | 4/2018 | Kane | G01N 33/004 |

* cited by examiner

SYSTEM AND METHOD FOR CONNECTING AN EXTERNAL DEVICE TO A GAS DETECTOR

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Gas detectors may be carried by workers and/or located throughout a work place and may detect gases in the environment. Gas detectors may be configured to alert a user and/or supervisor when a harmful gas or level of gas is detected. Gas detectors may also be configured to communicate sensed information to a monitoring station.

SUMMARY

In an embodiment, a gas detector may comprise a socket comprising a cable attachment configured to interface with an external device; and a holder configured to attach to the socket and to the external device, the holder comprising a first interface configured to attach to the socket of the gas detector; a second interface configured to attach to the external device; a first cable attachment located within the first interface, configured to attach to the gas detector; and a second cable attachment located within the second interface, configured to attach to the external device.

In an embodiment, a method for attaching an external device to a gas detector may comprise connecting a first cable attachment of a holder to a socket of the gas detector; securing a first interface of the holder to a portion of the socket of the gas detector, wherein the first interface surrounds the first cable attachment, and wherein securing the first interface occurs independently of connecting the first cable attachment; connecting a second cable attachment of the holder to the external device; and securing a second interface of the holder to a portion of the external device, wherein the second interface surrounds the second cable attachment, and wherein securing the second interface occurs independently of connecting the second cable attachment.

In an embodiment, a holder configured to attach to a gas detector may comprise a first interface configured to attach to a socket of the gas detector; a second interface configured to attach to an external device; a first cable attachment located within the first interface, configured to attach to the gas detector; and a second cable attachment located within the second interface, configured to attach to the external device.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
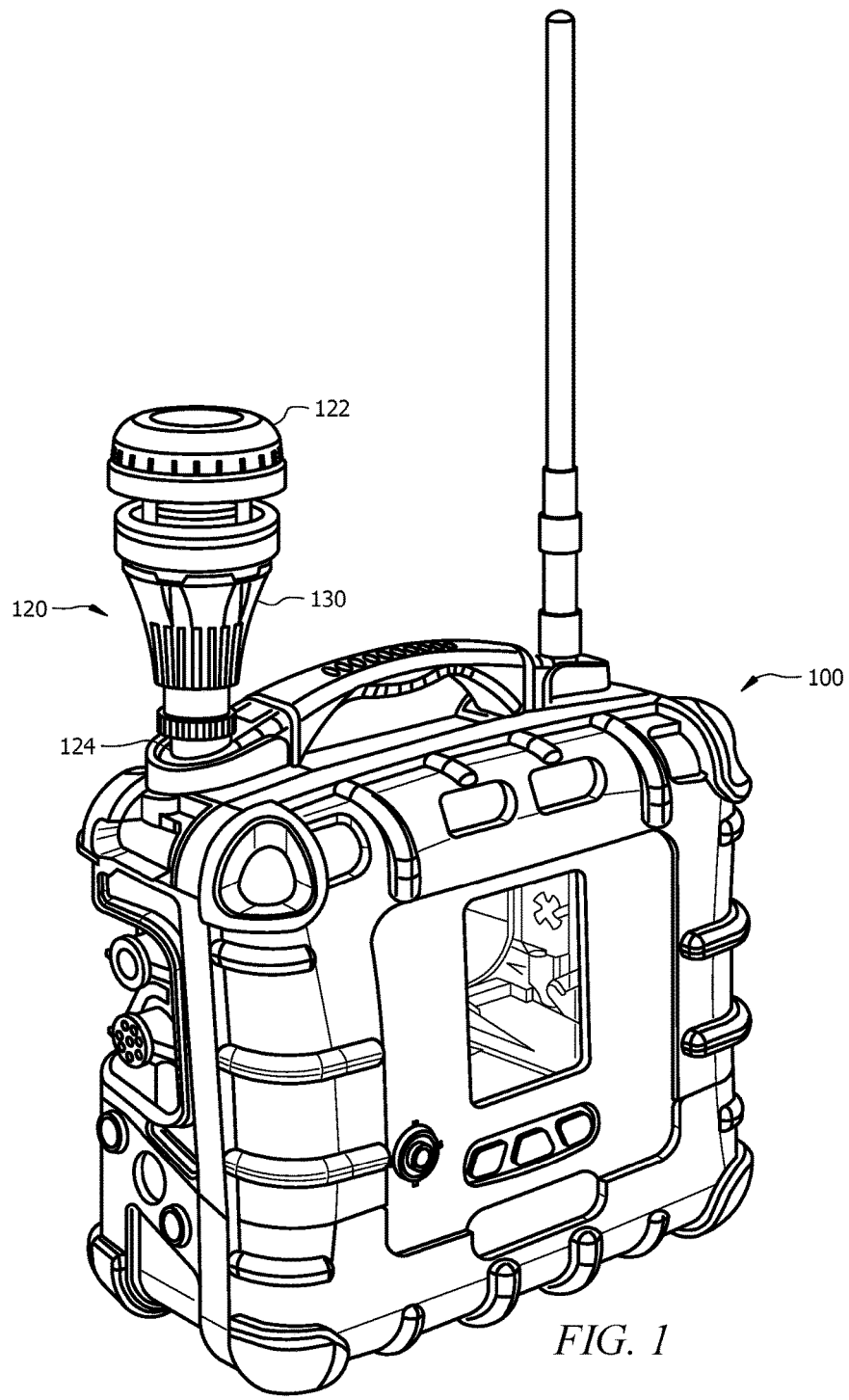
FIG. 1 illustrates a perspective view of a gas detector connected to an external assembly according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for securely attaching an external device to a gas detector. Typically, external devices may connect directly to a gas detector using standard cable terminals, such as multi-pin cables. However, this connection may be weak and easily broken or twisted, particularly if the gas detector is carried around in a work place. Additionally, the external devices may be interchanged and may be connected or disconnected by a user during their work, depending on the work environment of the user.

Embodiments of the disclosure include a holder configured to provide a secure attachment between the gas detector and an external device, such as an external sensor. The holder may also provide an easy connect and disconnect between the gas detector and the external device, such that a user may connect or disconnect during their work. The holder may protect the electrical and mechanical connection between the gas detector and the external device.

The holder may comprise threaded attachments surrounding cable attachments, where the threaded attachments may be controlled independently of the cable attachments. The threaded attachments may be made between molded parts, provided a stronger connection than the cable attachment alone.

Referring now to FIG. 1, a gas detector 100 is shown where the gas detector 100 may be a portable gas detector and may be configured to detect one or more characteristics of the surrounding environment, and may be configured to communicate one or more alerts to a user based on the detection. The gas detector 100 shown in FIG. 1 is an exemplary gas detector, where the gas detector 100 may include any type of detector device configured to allow for the connection of an external assembly 120. The gas detector 100 may comprise a socket 124 configured to receive and attach to the external assembly 120.

In some embodiments, the external assembly 120 may be attached to the socket 124 using a holder 130. The holder 130 may be configured to attach to the socket 124 and an external device 122, and may be configured to provide communication between the gas detector 100 (via the socket 124) and the external device 122. In some embodiments, the external device 122 may comprise a removable external sensor, such as a weather sensor.

Figure 2:
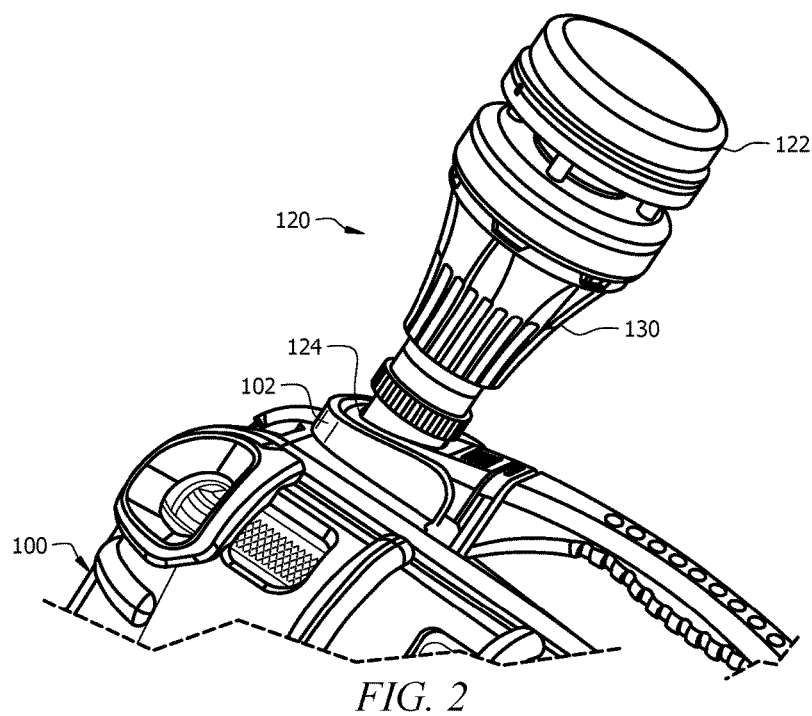
FIG. 2 illustrates another perspective view of a gas detector connected to an external assembly according to an embodiment of the disclosure.

FIG. 2 illustrates a detailed view of the external assembly 120 attached to the gas detector 100. The holder 130 may provide a secure connection between the external assembly 120 and the gas detector 100. Additionally, the holder 130 may allow for the socket 124 of the gas detector 100 to be recessed within the housing 102 of the gas detector 100, thereby protecting the socket 124, particularly if the gas detector 100 is used without the holder 130 and/or external device 122 attached.

Figure 3:
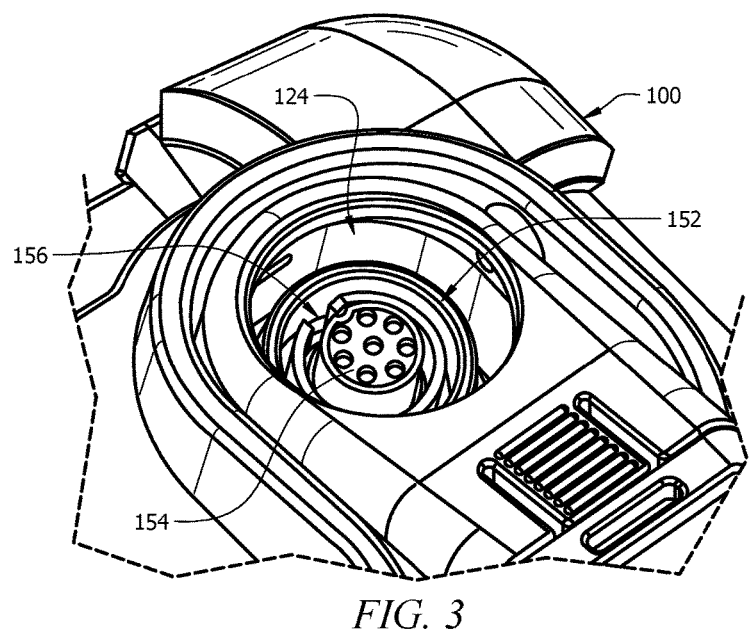
FIG. 3 illustrates a detailed view of a socket of a gas detector according to an embodiment of the disclosure.

FIG. 3 illustrates a detailed view of the socket 124 of the gas detector 100. The socket 124 may comprise a cable attachment 154 configured to receive (interface with) a multi-pin cable. The socket 124 may also comprise a threaded portion 152. In the embodiment shown in FIG. 3, the threaded portion 152 of the socket 124 may surround the cable attachment 154. As shown in FIG. 3, the threaded portion 152 may face outward from the cable attachment 154, but in an alternative embodiment, the threaded portion 152 may face in toward the cable attachment 154. The socket 124 may also comprise one or more alignment notches 156 configured to align any attachment with the cable attachment 154.

Figure 4:
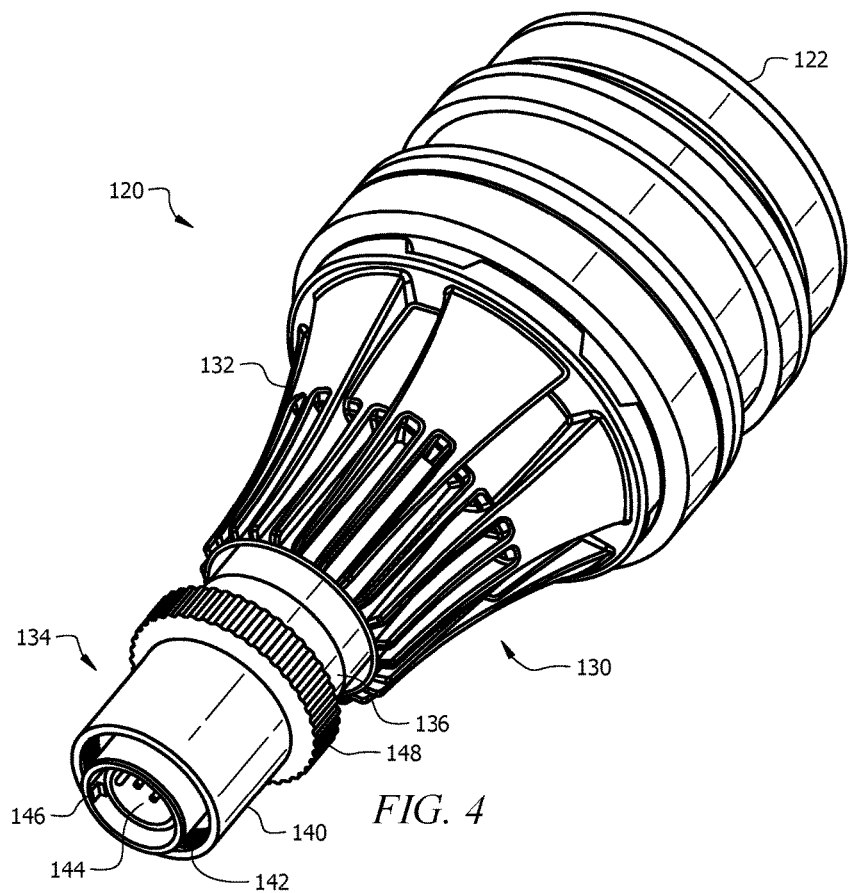
FIG. 4 illustrates a perspective view of an external assembly according to an embodiment of the disclosure.

FIG. 4 illustrates a detailed view of the external assembly 120 comprising the holder 130 and the external device 122. The holder 130 may comprise a first interface 134 located on one end of the holder 130 and a second interface 132 located on the opposite end of the holder 130. In the embodiments described herein, the first interface 134 may be configured to attach to the socket 124 of the gas detector 100 (as shown in FIG. 3). The second interface 132 may be configured to attach to the external device 122.

The holder 130 may comprise a first cable attachment 144 located within the first interface 134, where the first cable attachment 144 may be configured to attach to the cable attachment 154 of the gas detector 100. The first interface 134 may comprise one or more alignment notches 146, shoulders, pins, or recesses, which may correspond with the one or more corresponding alignment features, such as notches 156, of the socket 124. The first interface 134 may comprise a threaded portion 142 surrounding the first cable attachment 144, where the threaded portion 142 may be configured to thread onto the threaded portion 152 of the socket 124.

The first interface 134 of the holder 130 may comprise a first sleeve 140 configured to rotate with respect to (and independently of) the first cable attachment 144. The threaded portion 142 of the first interface 134 may be integrated into the first sleeve 140. As an example, once the first cable attachment 144 is attached to (or plugged into) the cable attachment 154 of the socket 124 (shown in FIG. 3), the first sleeve 140 may be rotated to engage the threaded portion 142 of the first sleeve 140 with the threaded portion 152 of the socket 124. The first sleeve 140 may comprise one or more grip elements 148, such as ridges, allowing the user to easily rotate the first sleeve 140.

Figure 5:
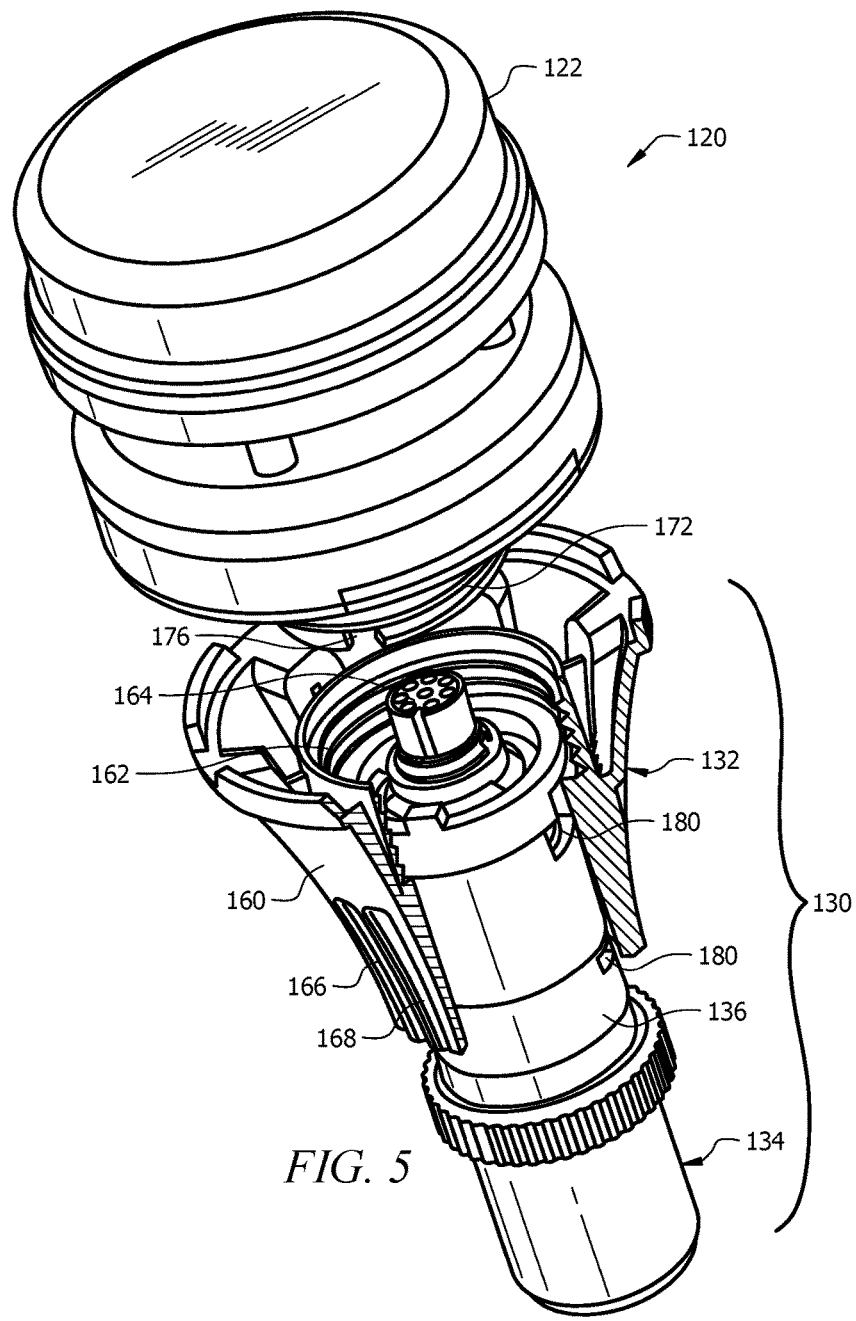
FIG. 5 illustrates a partial cut-away view of an external assembly according to an embodiment of the disclosure.
Figure 6:
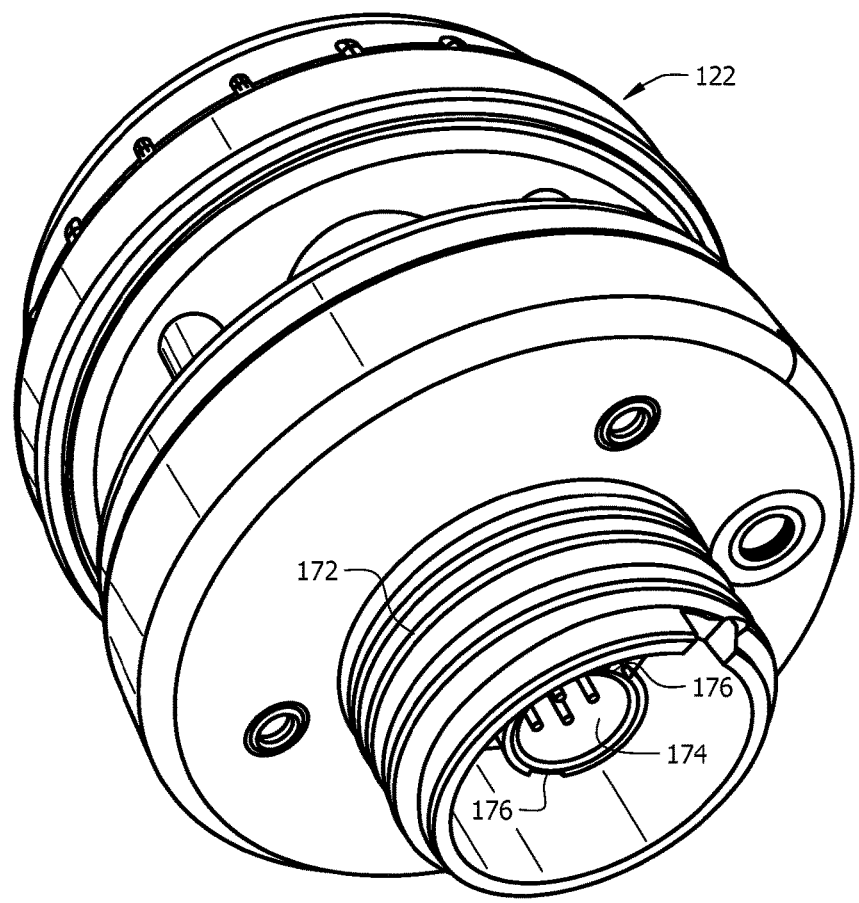
FIG. 6 illustrates a detailed view of an external device according to an embodiment of the disclosure.

FIG. 5 illustrates a partial cut-away view of the external assembly 120 comprising the holder 130 and the external device 122. As described above the second interface 132 of the holder 130 may attach to the external device 122. FIG. 6 illustrates a detailed view of the external device 122.

Referring to FIGS. 5 and 6, the holder 130 may comprise a second cable attachment 164 located within the second interface 132, where the second cable attachment 164 may be configured to attach to a cable attachment 174 of the external device 122. The second interface 132 may comprise one or more alignment notches 166, which may correspond with the one or more alignment notches 176 of the external device 122. The second interface 132 may comprise a threaded portion 162 surrounding the second cable attachment 164, where the threaded portion 162 may be configured to thread onto the threaded portion 172 of the external device 122.

The second interface 132 of the holder 130 may comprise a second sleeve 160 configured to rotate with respect to (and independently of) the second cable attachment 164. The threaded portion 162 of the second interface 132 may be integrated into the second sleeve 160. As an example, once the second cable attachment 164 is attached to (or plugged into) the cable attachment 174 of the external device 122, the second sleeve 160 may be rotated to engage the threaded portion 162 of the second sleeve 160 with the threaded portion 172 of the external device 122. The second sleeve 160 may comprise one or more grip elements 168, such as ridges, allowing the user to easily rotate the second sleeve 160. In some embodiments, the second sleeve 160 can comprise a flared or sloped outer profile. This may provide additional structural support to the external device 122 during use while also retaining the external device 122 in position through the threaded portion 162. The second sleeve 160 can extend towards the first interface 134 to help stabilize the overall connection during use.

In the embodiments described herein, the holder 130 may comprise a thru-cable 136 configured to connect the first interface 134 with the second interface 132. In some embodiments, the first sleeve 140 and the second sleeve 160 may rotate independently of the thru-cable 136. In some embodiments, the first sleeve 140 and the second sleeve 160 may be held onto the thru-cable via one or more channels

180. As shown in FIG. 5, the channels 180 may interface with the second sleeve 160, but similar channels may interface with the first sleeve 140.

Figure 7:
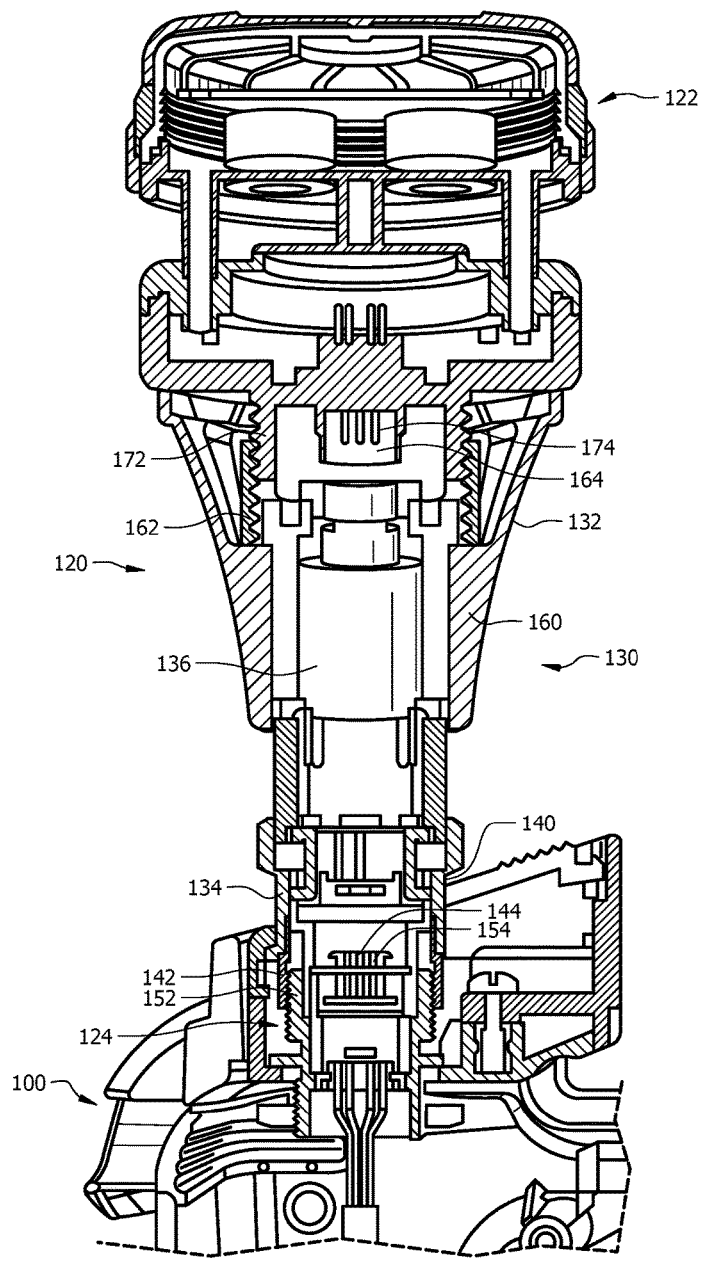
FIG. 7 illustrates a cross-sectional view of a gas detector connected to an external assembly according to an embodiment of the disclosure.

FIG. 7 illustrates a cross-sectional view of the external assembly 120 attached to the gas detector 100, the external assembly 120 and gas detector comprising all of the elements described in detail above, with reference to FIGS. 1-6.

Having described various devices and methods herein, exemplary embodiments or aspects can include, but are not limited to:

In a first embodiment, a gas detector may comprise a socket comprising a cable attachment configured to interface with an external device; and a holder configured to attach to the socket and to the external device, the holder comprising a first interface configured to attach to the socket of the gas detector; a second interface configured to attach to the external device; a first cable attachment located within the first interface, configured to attach to the gas detector; and a second cable attachment located within the second interface, configured to attach to the external device.

A second embodiment can include the gas detector of the first embodiment, wherein the socket comprises a multi-pin cable attachment configured to interface with the first cable attachment of the holder.

A third embodiment can include the gas detector of the first or second embodiments, wherein the first interface of the holder comprises a threaded portion configured to rotate independently of the first cable attachment.

A fourth embodiment can include the gas detector of the third embodiment, wherein the socket comprises a threaded portion configured to interface with the threaded portion of the first interface of the holder.

A fifth embodiment can include the gas detector of the third or fourth embodiments, wherein the threaded portion of the first interface of the holder is located on an outer perimeter of the first cable attachment.

A sixth embodiment can include the gas detector of any of the first to fifth embodiments, wherein the second interface comprises a threaded portion configured to rotate independently of the second cable attachment.

A seventh embodiment can include the gas detector of any of the first to sixth embodiments, wherein the holder further comprises a thru-cable configured to connect the first cable attachment to the second cable attachment, and also configured to provide communication between the socket of the gas detector and the external device.

In an eighth embodiment, a method for attaching an external device to a gas detector may comprise connecting a first cable attachment of a holder to a socket of the gas detector; securing a first interface of the holder to a portion of the socket of the gas detector, wherein the first interface surrounds the first cable attachment, and wherein securing the first interface occurs independently of connecting the first cable attachment; connecting a second cable attachment of the holder to the external device; and securing a second interface of the holder to a portion of the external device, wherein the second interface surrounds the second cable attachment, and wherein securing the second interface occurs independently of connecting the second cable attachment.

A ninth embodiment can include the method of the eighth embodiment, wherein securing the first interface of the holder to the portion of the socket comprises rotating a threaded portion of the first interface onto a threaded portion of the socket, wherein the threaded portion of the first interface rotates independently of the first cable attachment.

A tenth embodiment can include the method of the eighth or ninth embodiments, wherein securing the second interface of the holder to the portion of the external device comprises rotating a threaded portion of the second interface onto a threaded portion of the external device, wherein the threaded portion of the second interface rotates independently of the second cable attachment.

An eleventh embodiment can include the method of any of the eighth to tenth embodiments, further comprising communicating information between the gas detector and the external device via the first cable attachment, the second cable attachment, and a thru-cable located between the first cable attachment and second cable attachment.

A twelfth embodiment can include the method of any of the eighth to eleventh embodiments, further comprising aligning the first cable attachment with a cable attachment of the socket via one or more alignment notch; and aligning the second cable attachment with a cable attachment of the external device via one or more alignment notch.

In a thirteenth embodiment, a holder configured to attach to a gas detector may comprise a first interface configured to attach to a socket of the gas detector; a second interface configured to attach to an external device; a first cable attachment located within the first interface, configured to attach to the gas detector; and a second cable attachment located within the second interface, configured to attach to the external device.

A fourteenth embodiment can include the holder of the thirteenth embodiment, wherein the first interface comprises a threaded portion configured to rotate independently of the first cable attachment.

A fifteenth embodiment can include the holder of the thirteenth or fourteenth embodiments, wherein the second interface comprises a threaded portion configured to rotate independently of the second cable attachment.

A sixteenth embodiment can include the holder of any of the thirteenth to fifteenth embodiments, wherein the first cable attachment comprises a multi-pin cable attachment, and wherein the socket of the gas detector also comprises a multi-pin cable attachment.

A seventeenth embodiment can include the holder of any of the thirteenth to sixteenth embodiments, wherein the second cable attachment comprises a multi-pin cable attachment, and wherein the external device also comprises a multi-pin cable attachment.

An eighteenth embodiment can include the holder of any of the thirteenth to seventeenth embodiments, wherein the first interface comprises at least one alignment notch, and wherein the socket of the gas detector comprises at least one corresponding alignment notch.

A nineteenth embodiment can include the holder of any of the thirteenth to eighteenth embodiments, wherein the second interface comprises at least one alignment notch, and wherein the external device comprises at least one corresponding alignment notch.

A twentieth embodiment can include the holder of any of the thirteenth to nineteenth embodiments, further comprising a thru-cable configured to connect the first cable attachment to the second cable attachment, and also configured to provide communication between the socket of the gas detector and the external device.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A gas detector comprising:
   a socket comprising a cable attachment configured to interface with an external device; and
   a holder configured to attach to the socket and to the external device, the holder comprising:
      a first interface configured to attach to the socket of the gas detector;
      a second interface configured to attach to the external device;
      a first cable attachment located within the first interface, the first cable attachment comprising a first alignment notch and either a first plurality of pins or a first plurality of recesses configured to receive a plurality of pins in the gas detector, the first cable attachment configured to attach to the gas detector; and
      a second cable attachment located within the second interface, the second cable attachment comprising a second alignment notch and either a second plurality of pins or a second plurality of recesses configured to receive a plurality of pins in the external device, the second cable attachment configured to attach to the external device, wherein the second interface comprises a threaded portion configured to rotate independently of the second cable attachment.

2. The gas detector of claim 1, wherein the socket comprises a multi-pin cable attachment configured to interface with the first cable attachment of the holder.

3. The gas detector of claim 1, wherein the first interface of the holder comprises a threaded portion configured to rotate independently of the first cable attachment.

4. The gas detector of claim 3, wherein the socket comprises a threaded portion configured to interface with the threaded portion of the first interface of the holder.

5. The gas detector of claim 3, wherein the threaded portion of the first interface of the holder is located on an outer perimeter of the first cable attachment.

6. The gas detector of claim 1, wherein the holder further comprises a thru-cable configured to connect the first cable attachment to the second cable attachment, and also configured to provide communication between the socket of the gas detector and the external device.

7. A method for attaching an external device to a gas detector, the method comprising:
   connecting a first cable attachment of a holder to a socket of the gas detector,
   securing a first interface of the holder to a portion of the socket of the gas detector, wherein the first interface surrounds the first cable attachment, the first cable attachment comprising a first alignment notch and either a first plurality of pins or a first plurality of recesses configured to receive a plurality of pins in the gas detector, and wherein securing the first interface occurs independently of connecting the first cable attachment;
   connecting a second cable attachment of the holder to the external device; and
   securing a second interface of the holder to a portion of the external device, wherein the second interface surrounds the second cable attachment, the second cable attachment comprising a second alignment notch and either a second plurality of pins or a second plurality of recesses configured to receive a plurality of pins in the external device, and wherein securing the second interface occurs independently of connecting the second cable attachment.

8. The method of claim 7, wherein securing the first interface of the holder to the portion of the socket comprises rotating a threaded portion of the first interface onto a threaded portion of the socket, wherein the threaded portion of the first interface rotates independently of the first cable attachment.

9. The method of claim 7, wherein securing the second interface of the holder to the portion of the external device comprises rotating a threaded portion of the second interface onto a threaded portion of the external device, wherein the threaded portion of the second interface rotates independently of the second cable attachment.

10. The method of claim 7, further comprising communicating information between the gas detector and the external device via the first cable attachment, the second cable attachment, and a thru-cable located between the first cable attachment and second cable attachment.

11. The method of claim 7, further comprising aligning the first cable attachment with a cable attachment of the socket via the first alignment notch; and aligning the second cable attachment with a cable attachment of the external device via the second alignment notch.

12. A holder configured to attach to a gas detector, the holder comprising:
a first interface configured to attach to a socket of the gas detector;
a second interface configured to attach to an external device;
a first cable attachment located within the first interface, the first cable attachment comprising a first alignment notch and either a first plurality of pins or a first plurality of recesses configured to receive a plurality of pins in the gas detector, the first cable attachment configured to attach to the gas detector; and
a second cable attachment located within the second interface, the second cable attachment comprising a second alignment notch and either a second plurality of pins or a second plurality of recesses configured to receive a plurality of pins in the external device, the second cable attachment configured to attach to the external device,
wherein the second interface comprises a threaded portion configured to rotate independently of the second cable attachment.

13. The holder of claim 12, wherein the first interface comprises a threaded portion configured to rotate independently of the first cable attachment.

14. The holder of claim 12, wherein the first cable attachment comprises a multi-pin cable attachment, and wherein the socket of the gas detector also comprises a multi-pin cable attachment.

15. The holder of claim 12, wherein the second cable attachment comprises a multi-pin cable attachment, and wherein the external device also comprises a multi-pin cable attachment.

16. The holder of claim 12, wherein the first interface comprises at least one alignment notch, and wherein the socket of the gas detector comprises at least one corresponding alignment notch.

17. The holder of claim 12, wherein the second interface comprises at least one alignment notch, and wherein the external device comprises at least one corresponding alignment notch.

18. The holder of claim 12, further comprising a thru-cable configured to connect the first cable attachment to the second cable attachment, and also configured to provide communication between the socket of the gas detector and the external device.

* * * * *